United States Patent [19]

Simhoni et al.

[11] 4,278,079
[45] Jul. 14, 1981

[54] NEGATIVE HEEL PROTECTOR CUSHION

[76] Inventors: Orit Simhoni, 15455 NE. 6th Ave., North Miami, Fla. 33162; Donna H. Silver, 42 Perimeter Center, NE., Suite 220, Atlanta, Ga. 30346

[21] Appl. No.: 57,599

[22] Filed: Jul. 16, 1979

[51] Int. Cl.³ .......................... A61B 19/00; A61F 5/30
[52] U.S. Cl. ...................................... 128/149; 128/153
[58] Field of Search .................... 128/153, 149, 80 R, 128/165, 132 R

[56] References Cited

U.S. PATENT DOCUMENTS

| | | | |
|---|---|---|---|
| 2,085,296 | 6/1937 | Carey | 128/149 |
| 2,478,497 | 8/1949 | Morrison | 128/149 |
| 3,256,879 | 6/1966 | Hipps | 128/149 |
| 3,511,233 | 5/1970 | Holy, Jr. | 128/149 |
| 4,186,738 | 2/1980 | Schleicher | 128/153 |
| 4,197,845 | 5/1980 | Browning | 128/149 |

*Primary Examiner*—Kyle L. Howell
*Assistant Examiner*—C. W. Shedd

*Attorney, Agent, or Firm*—Barry L. Haley

[57] ABSTRACT

A therapeutic support device to prevent decubitus ulceration on the heel of the foot or to assist in the healing of a decubitus ulcer on the heel area comprising a resilient foot supporting body having a plurality of resilient, separable layers joined together in a stacked array by a pair of straps which can be adjusted in size for an individual foot, the straps holding the layers together and the support body to the foot itself. Each individual layer includes a central aperture such that the stacked array has a heel receiving central chamber. The device supports the foot of a supine or side-laying patient, while allowing the skin area of the heel to be free from contact with the bed or any surrounding surface. The number of layers may be selected to adequately support a particular weight foot; the upper layer may be replaced periodically for hygenic purposes. The top surface of the upper layer has a pocketed contour for improving pressure distribution and comfort of the patient. The holding straps that engage the foot may also be padded.

3 Claims, 4 Drawing Figures

NEGATIVE HEEL PROTECTOR CUSHION

BACKGROUND OF THE INVENTION

This invention relates generally to a device for use in enterostimal therapy, which deals with the prevention or treatment of bedsores. Bedsores are commonly formed on patients who must spend long periods of time in bed due to nonuniform pressure on the skin areas of the patient. The main treatment of bedsores is to provide pressure relief, especially in those areas of the body where greater pressures are normally experienced by the patient. Because of the shape and structure of the human body and the foot, bedsores on the heel area of the foot are common among some hospital patients, such as diabetics who have circulation problems and patients with paralysis or skin problems.

The prior art discloses devices used as orthopedic supports, such as abduction pillows. Such a device is shown in U.S. Pat. No. 4,135,504. In that device, the feet are supported on a single layer to prevent foot droop.

The present invention is directed specifically for the treatment or prevention of bedsores and provides an improved foot support which is not limited to orthopedic patients, but is useful for the treatment of any patient that might experience bedsores. The present invention allows a patient's heels to remain off and out of contact with the bed surface, whether in a prone, supine, or side-lying position. With the present invention, it also enables the patient to exercise dorsi-flexion or plantar-flexion at the ankle and flexion or extension at the knee or hip, because of the lightweight and noncumbersome structure of the present invention. Additional advantages of the present invention are the non-complex adjustment to accommodate different weights for different patients to insure enough layers for proper vertical support above the bed, without making the device exceedingly cumbersome on the foot; removable layers for periodic replacement due to hygenic considerations; and reduced pressure on the dorsal portion of the foot because of the crossed strap foot connection.

BRIEF DESCRIPTION OF THE INVENTION

A device for supporting a human foot of a prone, supine, or side-lying patient for suspending the heel area to prevent or treat decubitus ulceration on the heel. The device includes a plurality of resilient foam layers, each approximately one to two inches in height (or thickness) and preferably made from a product known under the trademark ZIMFOAM, the layers being joined together in a stacked, vertical array by a pair of web-like straps connected through each layer and issuing from the top of the device, the straps being a sufficient length for engagement around the dorsal area of the patient's foot.

The straps further include fabric-like fasteners, known under the trademark VELCRO, disposed near each free end for the length of each strap to fit the device to a particular foot. The straps are fastened together in a criss-cross pattern over the top of the foot.

Each individual foam layer includes a centrally located aperture which when joined together with other layers forms a central heel receiving chamber disposed through the entire thickness or height of the supporting device. Each layer may be quickly removed or installed on the straps for enlargement or reduction in the overall thickness of the support for variations necessitated by differences in weight or sizes of the patient's foot.

Each layer, and especially the top layer wherein portions or areas have some contact with the skin area adjacent the heel area to be suspended, includes a convoluted surface which applicant has found to provide better pressure distribution.

The top layer that contacts the patient's foot may be quickly removed and replaced when necessary for hygenic and cleanliness purposes.

The peripheral shape of the device is contoured to allow movement of the patient's foot or positioning of the patient's foot, either in a supine or side lying position.

The central aperture in each layer and therefore, in the entire heel supporting chamber, is sized to contact the foot in such a way that the heel area is free from any contact, either with the support itself or the bed surface. The aperture of the top layer may be individually cut to fit a particular patient's foot to insure noncontact of the heel area when placed within the central chamber.

It is an object of this invention to provide a foot supporting device that is noncomplex in construction and is useful for the treatment or prevention of bedsores on the heel area of a prone, supine, or side-lying patient.

It is another object of this invention to provide an enterostimal therapeutic device which may be adjusted to an individual patient's foot size to prevent decubitus ulceration of the heel area of a patient; and individually cut to accommodate a particular foot.

And yet another object of this invention is to provide a heel suspending device to prevent ulceration on the heel area that has changable layers of support for improved hygiene.

In accordance with these and other objects which will be apparent hereinafter, the instant invention will now be described with particular reference to the accompanying drawings.

PREFERRED EMBODIMENT OF THE INVENTION

Figure 1:
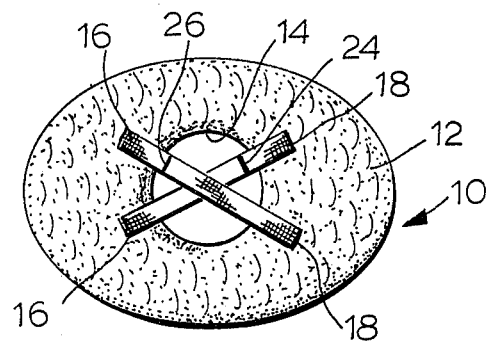
FIG. 1 shows a top plan view of the instant invention.
Figure 2:
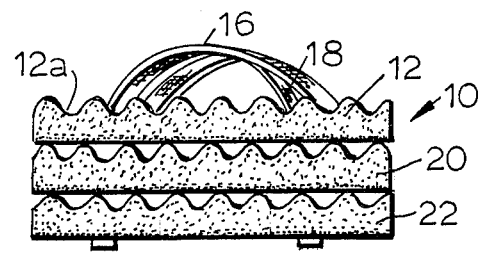
FIG. 2 shows a side elevational view of the instant invention.
Figure 3:
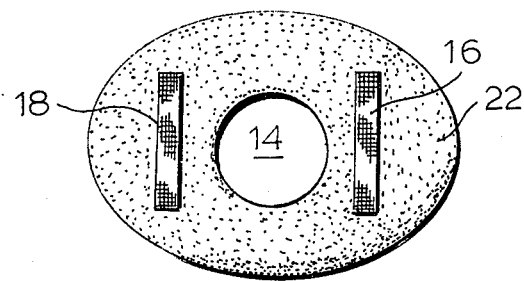
FIG. 3 shows a bottom plan view of the instant invention.

Referring now to the drawings and specifically FIGS. 1 and 2, the instant invention is shown generally at 10 comprised of three layers of foam 12, 20, and 22 in a stacked array, joined together by web-like straps 16 and 18 which have fabric connectors 24 and 26 (trademark VELCRO) for joining the free ends of the straps 16 and 18 together. The straps are disposed through small apertures in each layer 12, 20, and 22, and thus act to hold all three layers together. Each layer has a central aperture (shown as circular), forming an interior chamber 14 which is used to receive a heel. The upper surface of each layer, 12, 20, and 22 includes a plurality of undulations, such as 12a.

The support body 10 may be formed in any shape but a circular or elliptical shape is desirous to allow movement for different leg positions of the patient.

Figure 4:
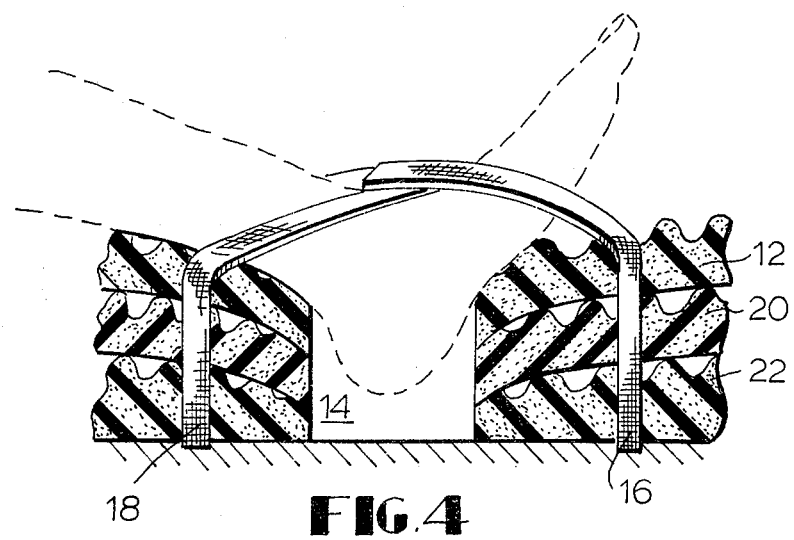
FIG. 4 shows a side elevational, cross-sectional view of a portion of the instant invention.

Referring now to FIG. 4, the present invention is shown strapped firmly but comfortably on a foot (dotted) with the heel area being suspended within the internal chamber 14, with sufficient clearance to avoid contact of the heel area with the bed or the inside wall of the internal chamber 14. The undulated surface 12a, which contacts other areas of the foot and ankle, acts to enhance pressure distribution and reduce pressure discomfort. Note that three separate support layers 12, 20, and 22 are shown. However, with the straps 16 and 18 unfastened, it is seen that the layers may be added or removed easily and quickly to increase or decrease the vertical thickness of the supporting device. Also, should the top layer (or any other layer) become soiled, any particular layer may be easily replaced. It is important that sufficient layers be provided such that the weight of the foot, regardless of the position of the leg and foot, support the heel area with plenty of space to prevent any exterior contact of the heel.

The VELCRO strips, which are attached at the free ends of web straps 16 and 18, have sufficient length to allow criss-cross overlapping of the straps, positioned over the foot, so that the supporting device is held firmly but comfortably to the foot. The straps may also be padded.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A therapeutic support device to prevent or assist in the healing of decubitus ulceration on the heel of the foot comprising:

a resilient body, said resilient body formed from a plurality of individual, resilient foam layers, each layer disposed in a stacked array, each of said layers having a substantially central aperture sized to receive the heel area of a foot with sufficient spacing around the heel area so that the heel area does not contact the surrounding surface formed from the aperture disposed within each layer, the layer apertures being stacked to form a single substantially central aperture in said resilient body, each of said layers having first, second and third and fourth strap receiving apertures, said first and second strap receiving apertures being disposed centrally on one side of central aperture, and said third and fourth apertures being disposed essentially on the opposite side of said central aperture in each layer; and a first strap connected through said first and second apertures in each of said layers and a second strap disposed through said third and fourth apertures in each of said layer, said first and second straps including an adjustable connecting means whereby the ends of said first, second, third and fourth strap can be removably connected to encircle the dorsal part of the foot when the heel is disposed within the central aperture.

2. A supporting device as in claim 1, wherein:
the upper surface of the top layer of said array has a plurality of pockets forming a wavy surface which engage the foot for increased comfort for the user.

3. A supporting device as in claim 1, wherein:
each of said individual foam layers has pockets forming a wavy upper surface.

* * * * *